(12) United States Patent
Joshi

(10) Patent No.: US 10,058,492 B2
(45) Date of Patent: Aug. 28, 2018

(54) ORAL CARE COMPOSITION COMPRISING BLEACHING AGENT

(71) Applicant: ROHM AND HAAS COMPANY, Philadelphia, PA (US)

(72) Inventor: Kinjalbahen Joshi, King of Prussia, PA (US)

(73) Assignee: Rohm and Haas Company, Philadelphia, PA (US)

( * ) Notice: Subject to any disclaimer, the term of this patent is extended or adjusted under 35 U.S.C. 154(b) by 31 days.

(21) Appl. No.: 15/024,637

(22) PCT Filed: Sep. 26, 2014

(86) PCT No.: PCT/US2014/057735
§ 371 (c)(1),
(2) Date: Mar. 24, 2016

(87) PCT Pub. No.: WO2015/048456
PCT Pub. Date: Apr. 2, 2015

(65) Prior Publication Data
US 2016/0220458 A1 Aug. 4, 2016

Related U.S. Application Data

(60) Provisional application No. 61/883,819, filed on Sep. 27, 2013.

(51) Int. Cl.
*A61K 8/22* (2006.01)
*A61K 8/42* (2006.01)
*A61K 8/02* (2006.01)
*A61K 8/81* (2006.01)
*A61Q 11/00* (2006.01)
*A61K 8/38* (2006.01)

(52) U.S. Cl.
CPC ............... *A61K 8/22* (2013.01); *A61K 8/022* (2013.01); *A61K 8/0216* (2013.01); *A61K 8/38* (2013.01); *A61K 8/42* (2013.01); *A61K 8/8147* (2013.01); *A61Q 11/00* (2013.01); *A61K 2800/412* (2013.01); *A61K 2800/592* (2013.01)

(58) Field of Classification Search
CPC ............. A61Q 11/00; A61K 8/22; A61K 8/11
USPC .................... 424/53, 447; 524/494
See application file for complete search history.

(56) References Cited

U.S. PATENT DOCUMENTS

| | | | |
|---|---|---|---|
| 4,988,500 A | 1/1991 | Hunter | |
| 5,785,957 A | 7/1998 | Losee | |
| 6,555,020 B1 | 4/2003 | Chadwick | |
| 6,759,030 B2 | 7/2004 | Kosti | |
| 2002/0197214 A1* | 12/2002 | Bublewitz | A61Q 11/00 424/53 |
| 2004/0063845 A1* | 4/2004 | Guzauskas | C08F 265/06 524/494 |
| 2006/0263307 A1* | 11/2006 | Robillard | B32B 15/085 424/53 |
| 2010/0310671 A1 | 12/2010 | Malotky | |
| 2011/0064683 A1 | 3/2011 | Jordan | |
| 2011/0064686 A1 | 3/2011 | Zhang | |
| 2011/0064688 A1 | 3/2011 | Jordan | |

OTHER PUBLICATIONS

DuPont, "Surlyn: thermoplastic resins." Product Information Aug. 2000; p. 1-2.*
Shah et al., "Blown films of nanocomposits prepared from low density polyethylene and a sodium ionomer of poly(ethlene-co-methacrylic acid)." Polymer 47 (2006) 6187-6201.*
International Search Report and Written Opinion relating to PCT/US20141057735 dated Nov. 17, 2014.

* cited by examiner

*Primary Examiner* — Walter E Webb
(74) *Attorney, Agent, or Firm* — McDonnell Boehnen Hulbert & Berghoff LLP

(57) ABSTRACT

The disclosed invention relates to a composition for delivery of a bleaching agent to an oral cavity. The composition is stable to environmental storage conditions, but upon subjection to highly aqueous conditions, releases the bleaching agent for use.

20 Claims, No Drawings

ORAL CARE COMPOSITION COMPRISING BLEACHING AGENT

CROSS-REFERENCE TO RELATED APPLICATION

This application is a U.S. national phase of International Application No. PCT/US2014/057735, filed Sep. 26, 2014, which claims priority to U.S. Provisional Application No. 61/883,819, filed Sep. 2, 2013, the disclosure of each of which is hereby incorporated by reference in its entirety.

BACKGROUND OF THE INVENTION

Field of the Invention

The invention relates to a composition for delivery of a bleaching agent. The composition includes a bleaching agent incorporated into a polymer, which is stable under slightly aqueous conditions, but dissolves when exposed to moderate or highly aqueous conditions, and/or mechanical action, releasing the bleaching agent Description of Related Art Teeth stained by foods and beverages can be whitened ("bleached") with oxidizing agents ("bleaching agents"). Most bleaching agents are chemically reactive oxidants and therefore challenging to stabilize in formulations such as toothpaste and oral rinses, A composition that stabilizes an bleaching agent in a polymer composition, such as a film, would be desirable in the oral care industry.

SUMMARY OF THE INVENTION

The invention provides a composition having:
an ethylene (meth)acrylic acid copolymer where at least a portion of the carboxylic acid groups are neutralized; and
about 5% to about 35% by weight of a bleaching agent.

The invention further provides a toothpaste formulation including:
a composition having an ethylene (meth)acrylic acid copolymer where at least a portion of the carboxylic acid groups are neutralized, and about 5% to about 35% by weight of a bleaching agent; and
a toothpaste base, The invention also provides a method for making a composition having:
an ethylene (meth)acrylic acid copolymer where at least a portion of the carboxylic acid groups are neutralized; and
about 5 to about 35% by weight of a bleaching agent.

The invention also provides a method for making a toothpaste formulation having;
a composition having an ethylene (meth)acrylic acid copolymer where at least a portion of the carboxylic acid groups are neutralized, and about 5%to about 35% by weight of a bleaching agent; and
a toothpaste base.

Also provided is a method for releasing a bleaching agent from:
a composition having:
an ethylene (meth)acrylic acid copolymer where at least a portion of the carboxylic acid groups are neutralized; and
about 5% to about 35% by weight of a bleaching agent, or from
a toothpaste formulation having:
a composition having an ethylene (rneth)acrylic acid copolymer where at least a portion of the carboxylic acid groups are neutralized, and about 5% to about 35% by weight of a bleaching agent; and
a toothpaste base.

These and other features and advantages of the present invention will be more fully understood from the following detailed description of the invention taken together with the claims. It is noted that the scope of the claims is defined by the recitations therein and not by the specific discussion of features and advantages set forth in the present description.

DETAILED DESCRIPTION OF THE INVENTION

The term "polymer" as used herein, is synonymous with "copolymer", "heteropolymer" and "alternating copolymer" and means a large molecule (macromolecule) composed of a repeating series of one or more alternating monomeric species. These sub-units are typically connected by covalent chemical bonds.

The term "substantially stable" means that the composition does not substantially fold, curl, dissolve or release a substantial amount of the bleaching agent under the prescribed environmental conditions. A small about of bleaching agent leaching may be observed under some conditions, but the composition is "substantially stable" if the composition retains greater than about 90% of the bleaching agent over an allotted period of time, or the composition remains substantially unchanged upon visual inspection.

The term "slightly aqueous conditions" means conditions or an environment where the moisture content is less than about 35% water by weight. Examples include a sealed container having a typical commercial toothpaste formulation.

The term "moderately aqueous conditions" means conditions or an environment where the moisture content is about 35% to about 50% water by weight.

The term "highly aqueous conditions" means conditions or an environment where the moisture content is greater than about 50% water by weight. Examples include an oral cavity or the conditions that occur when a toothpaste formulation is used to brush teeth.

The invention provides a composition having:
an ethylene (meth)acrylic acid copolymer where at least a portion of the carboxylic acid groups are neutralized; and
about 5 to about 35% by weight of a bleaching agent.

Ethylene (meth)acrylic acid copolymers can be used in a wide variety of applications including high-performance adhesives, flexible packaging films, pouches and in extrusion coating and extrusion lamination applications. "(Meth) acrylic", as used herein, means acrylic, methacrylic, or mixtures thereof. The free acid form of ethylene (meth) acrylic acid copolymers can be neutralized to the desired degree with a suitable base. Ethylene (meth)acrylic acid copolymers can be obtained with varying water solubility depending on the degree of neutralization. For example, complete water solubility is obtained when the (meth)acrylic acid moiety is completely neutralized with a stoichiometric amount of base. Partially neutralized EAA copolymers can be water dispersible, water sensitive, or water insensitive depending on the degree of neutralization.

At least a portion of the carboxylic acid groups in the (meth)acrylic acid component of the EAA copolymer are neutralized with a base, resulting in a salt. For example, the carboxylic acid groups may be neutralized with a base having a sodium cation, resulting in the sodium carboxylate salt. In another embodiment, the carboxylic acid groups may be neutralized with a base having a potassium cation to form a potassium carboxylate salt. The degree of neutralization may be between about 85% and about 100%, or between about 90% and about 100%, or between about 98% and about 100%. Increasing the degree of neutralization can increase the solubility of the composition in aqueous media. Those skilled in the art will recognize appropriate methods for determining degrees of neutralization. See, e.g., U.S. Pat. No. 3,472,825.

In some embodiments the ethylene (meth)acrylic copolymer is about 10% to about 30% (meth)acrylic acid by weight. In some embodiments, the copolymer is about 10% to about 15% (meth)acrylic acid, about 20% to about 25% (meth)acrylic acid, or about 25% to about 30% (meth)acrylic acid. In other embodiments, the copolymer is about 12% to about 17% (meth)acrylic acid, about 18% to about 22% (meth)acrylic acid, or about 23% to about 27% (meth)acrylic acid. In certain embodiments, the ethylene eth)acrylic copolymer is about 20.5% (meth)acrylic acid.

In some embodiments, the molecular weight of the ethylene (eth)acrylic acid copolymer is about 25 kg/mol to about 75 kg/mol. In one embodiment, the molecular weight of the ethylene (meth)acrylic acid copolymer falls within a range of about 25 kg/mol to about 35 kg/mol, about 35 kg/mol to about 45 kg/mol, about 45 kg/mol to about 55 kg/mol, about 55 kg/mol to about 65 kg/mol, or about 65 kg/mol to about 75 kg/mol.

In certain embodiments, the molecular weight of the ethylene (meth)acrylic acid copolymer is less than or equal to about 50 kg/mol.

In some embodiments, the ethylene (meth)acrylic acid copolymer is ethylene (meth)acrylic acid (EAA), In other embodiments, the ethylene (meth)acrylic acid copolymer's ethylene methacrylic acid (EMAA). In certain embodiments, the ethylene (meth)acrylic acid copolymer is a mixture of ethylene acrylic acid (EAA) and ethylene methacrylic acid (EMAA).

In some embodiments, the composition is in the form of a film or powder and has a water content of about 2% to about 20% by weight. In some embodiments, water content of the composition falls within a range of about 2% to about 5%, about 5% to about 10%, about 10% to about 15%, or about 15% to about 20% by weight. In certain embodiments, the composition has a water content of about 10% by weight.

The bleaching agent is a compound, mixture of compounds, or composition of one or more compounds able to whiten or disinfect a surface. In some embodiments, the bleaching agent is a peroxide. Peroxides can be inorganic salts or organic compounds having and/or capable of liberating hydrogen peroxide, which can be used as a whitening and/or disinfecting agent. The liberation of hydrogen peroxide can occur upon dissolution of a solid bleaching agent in water. Peroxides can also be used with a catalyst and/or activator, such as tetraacetylethylenediamine or sodium nonanoyloxybenzenesulfonate. A non-limiting list of peroxide compounds that can be used in the composition are: hydrogen peroxide, sodium percarbonate and corresponding salts, sodium perborate a id corresponding salts, peracetic acid, benzoyl peroxide, carbamide peroxide, and mixtures thereof. In certain embodiments, the bleaching agent is carbamide peroxide, which is a white crystalline solid, reacts with water to release hydrogen peroxide and urea, and is an approved bleach for oral care by the FDA.

In some embodiments, the bleaching agent is a chlorine containing compound, such as a hypochlorite salt. Particularly useful hypochlorite salts are sodium hypochlorite and calcium hypochlorite. Other useful bleaching agents are capable of liberating hydrogen peroxide, These compounds include organic peroxides, perborate salts, percarbonate salts, or a combinations thereof.

In some embodiments, the bleaching agent is used to whiten teeth. In other embodiments, the bleaching agent is used as a disinfectant. It has been shown that dilute solutions of sodium hypochlorite (about 0.05%) can be used as an antimicrobial agent in the treatment of periodontal diseases, such as gingivitis (De Nardo, R., Chiappe, V., Gómez, M, Romaneili, H. and Slots, J. (2012), Effects of 0.05% sodium hypochlorite oral rinse on supragingival biofilm and gingival inflammation, international Dental Journal, 62: 208-212, doi: 10.1111/j.1875-595X.2011.00111.x).

In some embodiments, the composition is in the form of a film. The film can be about 25 to about 250 microns in thickness. In some embodiments, the film can be about 50 to about 125 microns in thickness, about 100 to about 175 microns, or about 150 to about 250 microns. In certain embodiments, the film can be about 75 to about 125 microns in thickness. In other embodiments, the composition is in the form of a powder.

The film and/or the powder can include about 20% to about 35% of bleaching agent by weight. In some instances the amount of bleaching agent is about 20% to about 25%, or about 25% to about 30%, or about 30% to about 35% of the composition by weight. In certain embodiments, the composition includes about 24% to about 28% bleaching agent by weight.

In some embodiments, the composition is redispersible in aqueous solution. The film or powder can be added to an aqueous solution and used as a whitening and/or disinfecting solution. In some embodiments, the solution is an oral rinse.

The film can be segmented into fragments or flakes, or into a desired geometric shape, such as squares, rectangles or strips by die-cutting or slitting-and-die-cutting. The width and length of the film can vary according to the intended application. The dimensions of the film can vary from about 0.1 to about 10 millimeters in width and about 0.1 to about 10 millimeters in length. The ratio of length to width can be varied depending on the desired shape.

The invention further provides a toothpaste formulation including:

a composition having an ethylene (meth)acrylic acid copolymer where at least a portion of the carboxylic acid groups are neutralized, and about 5% to about 35% by weight of a bleaching agent; and a toothpaste base.

Commercial toothpaste typically has a water content of about 25% to about 35% by weight. The composition is stable below about 35% water content by weight, so the toothpaste formulation can have a toothpaste base having a water content of less than about 35% by weight. In some embodiments, the toothpaste base has about 28% to about 32% water content. in other embodiments the toothpaste base has about 30% water by weight.

In another embodiment, the composition is about 10% to about 30% of the toothpaste formulation by weight. in some embodiments, the composition is about 10% to about 15%, about 15% to about 20%, about 15% to about 20%, about 20% to about 25%, or about 25% to about 30% of the toothpaste formulation by weight.

In another embodiment, the tooth paste formulation further includes one or more additives. The additive can be any component added to obtain a desired property of the resulting formulation or a component added that interacts with the environment upon dissolution of the composition. in some instances, the additive can be a species that reacts with the bleaching agent, such as an activating agent. When the bleaching agent is incorporated into a composition, a id the composition is a component in an toothpaste base having the additive, the additive and bleaching agent do not react until the composition undergoes dissolution. This can allow for the stable storage of two reactive species in the same toothpaste formulation until the interaction of the bleaching agent and the additive is desired, Additives include coloring agents, sweetening agents, flavoring agents, breath-freshening agents, anti-microbial agents, activating agents, preservatives and mixture thereof.

Coloring agents are used in amounts effective to produce the desired color and include natural food colors and dyes suitable for food, drug and cosmetic applications (FD&C dyes). The coloring agents may be water-soluble, and include, in a non-limiting listing, Blue No. 1 (ethyl-[4-[[4-[ethyl-[(3-sulfophenyl)methyl]amino]phenyl]-(2-sulfophenyl)methylidene]-1-cyclohexa-2,5-dienylidene]-([3-sulfphenyl)methyl]azanium), FD&C Blue No. 2 (disodium salt of 5,5-indigotindisulfonic acid), Green No. 3 (ethyl-[4-[[4-[ethyl-[(3-sulfophenyl)methyl]amino]phenyl]-(4-hydroxy-2-sulfophenyl)methylidene]-1-cyclohexa-2,5-dienylidene]-[(3-sulfophenyl)methyl]azanium), Red No. 40 (disodium 6-hydroxy-5-((2-methoxy-5-methyl-4-sulfophenyl)azo)-2-naphthalenesulfonate) Red No. 3 (2-(6-Hydroxy-2,4,5,7-tetraiodo-3-oxo-xanthen-9-yl)benzoic acid) Yellow No. 5 (trisodium 1-(4-sulfonatophenyl)-4-(4-sulfonatophenylazo)-5-pyrazolone-3-carboxylate)) and Yellow No. 6 (Disodium 6-hydroxy-5-[(4-sulfophenyl)azo]-2-naphthalenesulfonate). In some embodiments, the coloring agent is titanium dioxide ($TiO_2$). The coloring agent may include a mixture of coloring agents. The amount of coloring agent used in the composition is determined depending on the color desired and the extent of the color desired.

In various embodiments, the additive can be a preservative, The choice of preservative will depend on the desired properties of the preservative. Various preservatives are known in the art, non-limiting examples include sodium benzoate and potassium sorbate. A preservative, or combination thereof, can be added in amounts of about 0.001 weight % to about 5 weight %, preferably of about 0.01 weight % to about 1 weight % of the film.

Flavoring agents that can be used include those known in the art, such as natural and artificial flavors, Flavoring oils may be chosen from natural and synthetic flavoring oils, aromatics, oleo resins, and extracts derived from plants, leaves, flowers, fruits etc., and combinations thereof. Flavoring oils can include: spearmint oil, cinnamon oil, peppermint oil, clove oil, bay oil, thyme oil, cedar leaf oil, oil of nutmeg, oil of sage, and oil of bitter almonds. Flavoring agents can be used individually or in admixture. Commonly used flavors include mints such as peppermint, artificial vanilla, cinnamon derivatives, coffee, cocoa, and various fruit flavors, whether employed individually or in admixture. Any flavoring or food additive approved for use in food processing may be used. The amount of flavoring agent used in the composition is determined depending on the type and desired strength of the flavor.

Sweetening agents include both natural and artificial sweeteners, Suitable sweetener include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). The amount of sweetening agent used in the composition is determined depending on the type and desired sweetness.

Breath-freshening agents can include zinc gluconate, zinc citrate and/or alpha ionone. These agents function in masking mouth odor and reducing volatile odor causing bacterial sulfur compounds. Also, several of the sweetening, flavoring and herbal agents described herein can be used as breath-freshening agents.

Anti-microbial agents include compounds that upon release from the composition interact with microbes in the environment, such as an antibacterial or antifungal agent. Examples include antibiotics, such as tricloscan, and anti-fungals, such as polyenes and azoles (imidazoles, triazoles and thiazoles).

Activating agents react with peroxide-based bleaching agents and aid in the liberation of hydrogen peroxide. They include, for example, tetraacetylethylenediamine and sodium nonanoyloxybenzenesulfonate.

The amount of the additive incorporated into the toothpaste formulation is determined depending on the type of additive and desired action of the additive following dissolution of the composition. The additive can be incorporated in the toothpaste formulation at a concentration of about 0.1% to about 5.0% by , eight. In some embodiments, the concentration of the additive is 0.1% to about 2.5% or about 3.0% to about 5.0% by weight. In some embodiments, the concentration of the additive is about 1.0 to about 3.0% of the formulation by weight.

The invention also provides a method for making a composition having:
an ethylene (meth)acrylic acid copolymer where at least a portion of the carboxylic acid groups are neutralized; and
about 5 to about 35% by weight of a bleaching agent, the method including:
forming a mixture of ethylene (meth)acrylic acid copolymer in water;
neutralizing the mixture;
adding a bleaching agent to the neutralized first mixture; and
removing water from the neutralized mixture to provide a solid composition.

The invention also provides a method for making a toothpaste formulation having:
a composition having an ethylene (meth)acrylic acid copolymer where at least a portion of the carboxylic acid groups are neutralized, and about 5% to about 35% by weight of a bleaching agent; and
a toothpaste base,
the method including:
forming a mixture of ethylene (meth)acrylic acid copolymer in water;
neutralizing the mixture;
adding a bleaching agent to the neutralized mixture;
removing water from the neutralized mixture to provide a solid composition; and
adding the solid composition to a toothpaste base.

In some embodiments, the removal of water includes casting the neutralized mixture to provide a film. In another embodiment, the removal of water includes freeze-drying the combined mixture to provide a powder.

Neutralizing can be accomplished with an aqueous base so that the mixture obtains a pH of 8.0 or greater. In certain embodiments, the mixture is neutralized at a pH of about 10.5. Bases can include alkali hydroxides, carbonates and percarbonates.

In another embodiment, the water removal includes casting the combined mixture to provide a film. The casting can involve forming a layer of the neutralized mixture and removing water. Water removal can occur at ambient temperature, or in some instances, the water removal occurs at elevated temperature, such as about 40° C. Water removal can also be accomplished at temperatures in the range of about 40° C. to about 60° C., or about 60° C. to about 80° C. In some embodiments, water removal is performed under vacuum.

The film composition can be cast to provide a film of about 50 to about 250 microns thick, or about 50 to about 100 microns, or about 150 to about 250 microns, or about 100 to about 150 microns. The solid composition can be fragmented as described herein before being added to the toothpaste base.

The invention further provides a method for releasing a bleaching agent from:
a composition having:
an ethylene (meth)acrylic acid copolymer where at least a portion of the carboxylic acid groups are neutralized; and
about 5% to about 35% by weight of a bleaching agent,
by subjecting the composition to a moderate to highly aqueous environment, or mechanical action.

In some embodiments, the composition is a component in a toothpaste formulation having a toothpaste base as described herein, which includes less than about 35% water by weight.

In some embodiments, the mechanical action includes the brushing of teeth.

In some embodiments, the wet environment is the addition of water to the composition or a toothpaste formulation. in other embodiments, the wet environment is an oral cavity.

In some embodiments, the composition or formulation incorporates an additive that is released upon subjection to the mechanical action or wet environment. The additive can be inert or interact with the bleaching agent or environment as desired.

EXAMPLES

Example 1

Film Composition

A dispersion of ethylene acrylic acid copolymer (20.5% acrylic acid, 79.5% ethylene; melt flow index=300; molecular weight<50 kg/mol; $T_m$=77° C. ) is neutralized to about pH 10.5 with sodium hydroxide. Carbamide peroxide is added, and the resulting mixture is 90% ethylene acrylic acid copolymer (~24-30% solid concentration level) and 10% carbamide peroxide by weight. The mixture is cast (250 microns wet) and dried at 40° C. for 1 h. The composition of the resulting 75 micron film is 10% water, 63.52% ethylene/acrylic acid copolymer and 26.47% carbamide peroxide by weight.

Example 2

Stability of Composition in Film and Release Upon Redispersion

Redispersibility of the film with and without the bleaching agent is tested. A film is prepared according to Example 1, except that carbamide peroxide is not added. The resulting film, and the film from Example 1 (containing peroxide) are added to water. The ethylene/acrylic acid co-polymer based film without peroxide does not redisperse in water, even with agitation, But the film composition with carbamide peroxide rapidly redisperses, yielding an opaque aqueous mixture.

Example 3

Release Upon Redispersion of a Powder Composition

A composition is made according to Example 1, except that the mixture is freeze dried instead of being cast and dried. The resulting powder (0.2 g) is added to 25 ml of water in glass beaker, add stirred @450 rpm using stir bar. A peroxide testing strip confirms the presence of hydrogen peroxide in the mixture.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A composition in the form of a powder comprising:
ethylene (meth)acrylic acid copolymer where at least a portion of the carboxylic acid groups are neutralized, wherein the molecular weight of the ethylene (meth) acrylic acid copolymer is about 25 kg/mol to about 75 kg/mol; and
about 5% to about 35% by weight of a bleaching agent.

2. The composition of claim 1, where the molecular weight of the ethylene (meth)acrylic acid copolymer is less than or equal to about 50 kg/mol.

3. The composition of claim 1, where the composition has a water content of about 5% to about 15% by weight.

4. The composition of claim 1, where the bleaching agent is a compound capable of liberating hydrogen peroxide.

5. The composition of claim 1, where the bleaching agent is selected from an organic peroxide, perborate salt, percarbonate salt, or a combination thereof.

6. The composition of claim 1, where the copolymer comprises about 10% to about 30% (meth)acrylic acid by weight.

7. The composition of claim 1, where the composition is in the form of a film.

8. The composition of claim 7, where the film is about 50 to about 100 microns in thickness.

9. The composition of claim 1, where the composition is in the form of a powder.

10. The composition of claim 1, where the composition is redispersible in aqueous solution.

11. A toothpaste formulation comprising the composition of claim 1 and a toothpaste base.

12. The toothpaste formulation of claim 11, where the composition is about 10% to about 30% by weight of the formulation.

13. The toothpaste formulation of claim 11, where the toothpaste base comprises less than about 35% water by weight.

14. The toothpaste formulation of claim 11, where the formulation further comprises an additive.

15. The composition of claim 14, where the additive is selected from a sweeting agent, flavoring agent, coloring agent, herbal agent, botanical agent, vitamin, anti-oxidant, or mixture thereof.

16. A composition according to claim 2, wherein
the composition has a water content of about 5% to about 15% by weight;

the bleaching agent is selected from an organic peroxide, perborate salt, percarbonate salt, or a combination thereof; and the copolymer comprises about 10% to about 30% (meth)acrylic acid by weight.

17. A composition according to claim 16, where the composition is in the form of a film.

18. A composition of claim 17, where the film is about 50 to about 100 microns in thickness.

19. A composition according to claim 16, where the composition is in the form of a powder.

20. A toothpaste formulation comprising
a toothpaste base comprising less than about 35% water by weight; and
from about 10% to about 30% by weight of composition comprising:
   ethylene (meth)acrylic acid copolymer wherein
      at least a portion of the carboxylic acid groups are neutralized,
      the molecular weight of the ethylene (meth)acrylic acid copolymer is less than or equal to about 50 kg/mol; and
      the copolymer comprises about 10% to about 30% (meth)acrylic acid by weight; and
   about 5% to about 35% by weight of a bleaching agent, wherein the bleaching agent is selected from an organic peroxide, perborate salt, percarbonate salt, or a combination thereof.

* * * * *